(12) United States Patent
Brennan (10) Patent No.: US 9,138,514 B2
(45) Date of Patent: Sep. 22, 2015

(54) MEDICAL SUCTION SYSTEM AND DISPOSABLE CONTAINER

(71) Applicant: H. George Brennan, Newport Beach, CA (US)

(72) Inventor: H. George Brennan, Newport Beach, CA (US)

( * ) Notice: Subject to any disclaimer, the term of this patent is extended or adjusted under 35 U.S.C. 154(b) by 0 days.

(21) Appl. No.: 13/748,488

(22) Filed: Jan. 23, 2013

(65) Prior Publication Data

US 2013/0331805 A1  Dec. 12, 2013

Related U.S. Application Data (63) Continuation-in-part of application No. 13/494,776, filed on Jun. 12, 2012.

(51) Int. Cl.
*A61M 1/00* (2006.01)

(52) U.S. Cl.
CPC .............. *A61M 1/0001* (2013.01); *A61M 1/008* (2013.01); *A61M 1/0023* (2013.01); *A61M 1/0031* (2013.01); *A61M 2205/8206* (2013.01); *A61M 2209/088* (2013.01); *A61M 2210/0618* (2013.01)

(58) Field of Classification Search
USPC .............................. 604/319, 327; 128/202.16
See application file for complete search history.

(56) References Cited

U.S. PATENT DOCUMENTS

| | | | |
|---|---|---|---|
| 4,392,858 A * | 7/1983 | George et al. | 604/133 |
| 4,403,611 A | 9/1983 | Babbitt et al. | |
| 4,828,546 A * | 5/1989 | McNeil et al. | 604/73 |
| 4,883,465 A | 11/1989 | Brennan | |
| 4,994,084 A | 2/1991 | Brennan | |
| 5,011,474 A | 4/1991 | Brennan | |
| 5,045,075 A | 9/1991 | Ersek | |
| 5,318,548 A * | 6/1994 | Filshie | 604/319 |
| 5,514,179 A | 5/1996 | Brennan | |
| 5,931,852 A | 8/1999 | Brennan | |
| 6,936,037 B2 | 8/2005 | Bubb et al. | |
| 6,951,553 B2 | 10/2005 | Bubb et al. | |
| 7,553,306 B1 | 6/2009 | Hunt et al. | |
| 2002/0058915 A1 | 5/2002 | Wakabayashi | |
| 2003/0040687 A1 | 2/2003 | Boynton et al. | |
| 2003/0093041 A1 | 5/2003 | Risk, Jr. et al. | |
| 2004/0006319 A1 | 1/2004 | Lina et al. | |

(Continued)

OTHER PUBLICATIONS

International Search Report and Written Opinion of International Application No. PCT/US2013/044982; 7 Pages.

(Continued)

*Primary Examiner* — Susan Su
(74) *Attorney, Agent, or Firm* — Stetina Brunda Garred & Brucker (57) ABSTRACT

A portable, adjustable disposable medical suction system and method of use is disclosed. The system includes a delivery device to provide a conduit from a surgical site on a patient to the portable, adjustable medical suction system. The suction system may be a battery powered vacuum pump with one or more different adjustments directed to a strength of the vacuum, duration of the vacuum and interval between suction. The delivery device may be an intranasal tampon device or a tube inserted into the surgical site. During surgery and recovery at a surgical center or hospital, the vacuum source attached to the delivery system may be an industrial type vacuum source. Upon discharge, the suction system can be connected to the delivery system so that bleeding can be resolved by the patient in the comfort of his/her own home. The system and method of use is safer and mitigates body fluid borne contamination.

4 Claims, 7 Drawing Sheets

(56) References Cited

U.S. PATENT DOCUMENTS

| | | |
|---|---|---|
| 2004/0064923 A1 | 4/2004 | Gzybowski |
| 2006/0122575 A1 | 6/2006 | Wakabayashi |
| 2007/0010797 A1* | 1/2007 | Nishtala et al. ............... 604/540 |
| 2007/0027433 A1* | 2/2007 | Garcia et al. ................. 604/319 |
| 2007/0179460 A1* | 8/2007 | Adahan ......................... 604/319 |
| 2008/0108960 A1* | 5/2008 | Shapland et al. ............. 604/321 |
| 2008/0200905 A1* | 8/2008 | Heaton et al. ................ 604/543 |
| 2009/0062755 A1* | 3/2009 | Burgess et al. ............... 604/326 |
| 2009/0248058 A1 | 10/2009 | Kotler |
| 2010/0179493 A1* | 7/2010 | Heagle et al. ................ 604/313 |
| 2014/0163488 A1* | 6/2014 | Vaillancourt et al. ......... 604/319 |

OTHER PUBLICATIONS

Victoria Reitz, A Few Guidelines for Selecting Filters, Article from Web site, Jul. 1, 2005, 8 pages, published by Penton Media Inc. (2011).

Google, Nalge Nunc Vacuum Pumps, Hand-operated, Nalgene 6131-0010 Small Pump w/ Free UPS, Google product search, Jan. 12, 2012, 2 pages.

Wikipedia, Peristaltic Pump, Article from Web site, Jan. 7, 2012, 7 pages, Wikipedia.

\* cited by examiner

MEDICAL SUCTION SYSTEM AND DISPOSABLE CONTAINER

CROSS-REFERENCE TO RELATED APPLICATIONS

This application is a continuation in part application of U.S. patent application Ser. No. 13/494,776 filed on Jun. 12, 2012, the entire contents of which are expressly incorporated herein by reference.

STATEMENT RE: FEDERALLY SPONSORED RESEARCH/DEVELOPMENT

Not Applicable

BACKGROUND

The embodiments disclosed herein relate to a portable, adjustable disposable medical suction system and method of use.

Nasal hemorrhaging or bleeding is topically arrested by forcing a plurality of small cylinders or absorbent material into the nasal cavity until sufficient pressure is created to provide a nasal hemostat. The nasal packing procedure is delicate and must apply adequate pressure to relieve and eliminate bleeding. Unfortunately, the nasal packing procedure is often painful for the patient. Moreover, the packing material may be inadvertently dislodged from the intended area. As a result the packing material must be reset thereby causing additional pain, to the patient.

Moreover, when nasal bleeding has stopped, the nasal packing must be removed which is also a very painful process. If nasal bleeding is a result of surgery, then the patient must remain at the surgical center or hospital until the bleeding is under control thereby increasing medical costs. Other methods and devices for arresting nasal bleeding have been introduced into the marketplace. These other methods are described in U.S. Pat. Nos. 4,883,465 and 5,011,474, tire entire contents of which are expressly incorporated herein by reference. Unfortunately, these other methods and devices require the patient to remain at the surgical center or hospital after surgery until nasal bleeding has ceased thereby extending the time and cost for the patient and the surgical center or hospital. The reason that the patient must remain at the surgical center or hospital is that these methods and devices aspirate bodily fluid with a vacuum provided by a central vacuum system of the surgical center or hospital. If the bodily fluid continues to flow out of the wound, the patient needs to be connected to the central vacuum system of the surgical center so that the bodily fluid can be continuously aspirated.

Additionally, when a patient undergoes any invasive surgery, the surgical site will have internal bleeding. After suturing the opening of the surgical site, the fluid from the internal bleeding must be removed. To this end, a tube with a plurality of apertures at the distal portion of the tube is placed within the patient at the surgical site. The tube exits through the opening of the surgical site. The tube provides a conduit through which the bodily fluid from the internal bleeding can flow out of the patient. A vacuum is created oftentimes by use of a resilient drain bulb. The opposite end of the tube is connected to the drain bulb. The drain bulb is manually squeezed to eliminate air from the interior of the bulb and then connected to the opposite end of the tube. Due to the resiliency of the bulb, a vacuum is created which is applied to the tube and aspirate the bodily fluid. Unfortunately, the operation of the drain bulb is unsanitary and typically unsafe. The patient or caregiver (layperson) must remember to squeeze the drain bulb right before attaching the drain bulb to the tube. If the patient or caregiver fails to properly install the drain bulb, then the patient's bodily fluids will not be aspirated. Also, if air is aspirated from the surgical site, the drain bulb will expand too rapidly and not aspirate bodily fluid from the surgical site.

Accordingly, there is a need in the art for an improved device and method for collecting blood or bodily fluids.

BRIEF SUMMARY

The embodiments disclosed herein address the needs discussed above, discussed below and those that are known in the art.

A portable, adjustable disposable medical suction system and method of use are disclosed. The system includes a vacuum pump capable of creating suction within a tube. A first portion of the tube is placed in the area of the surgical site. A second portion of the tube may be connected to the vacuum pump. The vacuum pump is capable of aspirating blood and bodily fluid from the surgical site, into the tube and into a disposable bag. The vacuum pump is programmable and may also be manually operated based on the needs of the patient's body. The bag may be self-sealing so that upon disconnection from the tube or the vacuum pump, the bodily fluid collected in the bag does not spill and contaminate the surrounding area. The self-sealing bag can be placed in a red colored bag clearly marked as a bio hazard for later disposal by the patient. The patient can easily install a new empty bag to the tube or vacuum pump. This system can be operated by the patient or caregiver at home after discharge due to its ease of use. Hence, the patient can be discharged earlier from the surgical center or hospital and does not need to remain at the surgical center or hospital until bleeding or fluid collection has ceased. Accordingly, the system and methods of use discussed herein reduce cost for the patient and surgical center or hospital. After being discharged for one or two days, the patient may call and inform the doctor of the quantity of bodily fluid collected as well as the type (e.g. color, consistency, etc.) of the bodily fluid collected so that the doctor can determine the patient is healing properly.

More particularly, a portable medical fluid management system for withdrawing bodily fluid from a patient after surgery is disclosed. The system may comprise an elongate tube defining a first portion having a plurality of apertures and a second opposite portion. The first portion may be disposed under the skin of the patient at a surgical site for withdrawing bodily fluid from the surgical site. The second portion may be disposed outside of the skin of the patient. The first and second portions may be in fluid communication with each other. The system may also comprise a collection container which may be removably attachable to the second portion of the elongate tube. The system may also comprise a portable vacuum source attached to the second portion for creating suction in the elongate tube so that bodily fluid under the skin at the surgical site is removed from the surgical site and transferred to the collection container. As discussed further below, the collection container provides for a sanitary and easy to use system for those who might use the system such as doctors, nurses, patients, caregivers and laypersons.

The portable vacuum source may be operated with a battery. However, it is also contemplated that the portable vacuum source may be powered by a conventional AC or DC power source. The portable vacuum source may have a first control knob for adjusting strength of the suction of the vacuum source. The strength of the section of the vacuum source may be adjusted by speeding up the motor of the vacuum source or slowing down the motor of the vacuum source. The portable vacuum source may have a second control knob for adjusting the duration of time of suction of the vacuum source. For example, the motor of the vacuum source may be turned on for a period of time then turned off cyclically. The portable vacuum source may have a third control knob for adjusting spacing or timing interval between successive application of suction by the portable vacuum source. The strength of the suction of the vacuum source, the duration of time of suction of the vacuum source and the timing interval adjustment may be programmed into a chip that regulates the power to the motor from a battery or electrical source.

In another aspect, a portable nasal tampon for allowing a patient to breathe and to withdraw blood/bodily fluid from a nasal cavity during and after surgery at a nasal area of the patient is disclosed. The portable nasal tampon may also be utilized during and/or after trauma, epistaxis (i.e., nosebleed) or sinus/nasal surgery event to collect blood or bodily fluid. The portable nasal tampon may comprise first and second absorbent pads for absorbing blood or bodily fluid; a first breathing tube extending from opposed distal ends of the first absorbent pad through which the patient may breathe when the first absorbent pad is disposed within the nasal cavity of the patient; a second breathing tube extending from opposed distal ends of the second absorbent pad through which the patient may breathe when the second absorbent pad is disposed within the nasal cavity of the patient; a first suction tube with a first distal end portion disposed within the first absorbent pad for providing a conduit through which blood or bodily fluid is traversed out of the nasal cavity; a second suction tube with a first distal end portion disposed within the second absorbent pad for providing a conduit through which blood or bodily fluid is traversed out of the nasal cavity; a travel sized collection container in communication with the first and second suction tubes for collecting blood or bodily fluid traversed through the first and second suction tubes from the first and second absorbent pads; and a vacuum source in communication with the first and second suction tubes for extracting blood or bodily fluid out of the first and second absorbent pads and traversing the blood or bodily fluid through the first and second suction tubes into the collection container. The portable nasal tampon may also be attached to a strap wrapped about a body part of the patient such as the arm, neck, waist or chest. The strap is used to hold up the portable nasal tampon so that the weight of the portable nasal tampon does not cause the portable nasal tampon to slip out of the patient's nasal cavity. Additionally or alternatively, the portable nasal tampon may have an inflatable cuff as described in U.S. Pat. No. 4,883,465, the entire contents of which are expressly incorporated herein by reference. The inflatable cuff prevents backflow of bodily fluids or blood into the throat and ultimately into the stomach and airway of the patient.

The portable nasal tampon may further comprise a filter disposed upstream of the vacuum source.

The travel sized collection container may be a flexible bag capable of receiving up to 8 fluid ounces.

The vacuum source may weigh less than 1 lb, so that the vacuum source can be characterized as a travel sized vacuum source. The vacuum source may also be a battery operated vacuum source.

The portable nasal tampon may further comprise a Y connector with a connector that is capable of connecting a vacuum source connector that is common among a central vacuum source at a surgical center or hospital and a battery operated vacuum source.

In another aspect, a method of minimizing pain and discomfort associated with bleeding due to a nasal surgery is disclosed. The method may comprise the steps of installing left and right absorbent pads into left and right nostrils of a patient wherein left and right breathing tubes are positioned within the left and right nostrils to allow the patient to breathe through his or her nostrils during surgery, during recovery and after discharge from a surgical center or hospital; connecting left and right suction tubes to a first vacuum source located within a surgical room of the surgical center or hospital; conducting nasal surgery on the patient; disconnecting the suction tubes from the first vacuum source; transporting the patient to a recovery room; connecting left and right suction tubes to a second vacuum source located within the recovery room of the surgical center or hospital; upon discharge of the patient from the surgical center or hospital, disconnecting the left and right suction tubes from the second vacuum source and instructing the patient to connect the suction tubes to a portable vacuum source; and maintaining the left and right absorbent pads in the left and right nostrils of the patient during surgery, during recovery and after discharge.

In the method, the portable vacuum source may be a battery operated vacuum pump.

In the method, the suction tubes may be connected to a single common tube wherein the single common tube has a connector capable of being connected to the portable vacuum source, first vacuum source and second vacuum source without removing the left and right pads from the left and right nostrils of the patient.

BRIEF DESCRIPTION OF THE DRAWINGS

These and other features and advantages of the various embodiment disclosed herein will be better understood with respect to the following description and drawings, in which like numbers refer to like parts throughout, and in which.

DETAILED DESCRIPTION

Referring now to the drawings, a portable, adjustable disposable medical suction system 200 (see FIG. 1) and method of use is disclosed. The system is described in relation to implementation for nasal surgery and also an invasive surgical procedure but may be utilized in other contexts as well.

An intranasal tampon device 10 (see FIG. 3) may be utilized during surgery, during recovery and after discharge so that pain and discomfort associated with nasal bleeding is minimized. The intranasal tampon device 10 may also have an inflatable cuff 46 (see FIG. 5) as described in U.S. Pat. No. 4,883,465 for the purposes of preventing blood and bodily fluid from flowing back through the throat and ultimately into the stomach or airway of the patient. The entire contents of U.S. Pat. No. 4,883,465 are incorporated herein by reference. After discharge, the device 10 remains in the nasal cavity and is not removed. While the device 10 remains in the nasal cavity, the device 10 is coupled to the portable, adjustable disposable medical suction system 200. In this regard, patient comfort is maximized in that the patient can enjoy mobility and be discharged earlier from a surgical facility (i.e., surgical center or hospital).

During nasal surgery and during recovery at the surgical center or hospital, the intranasal tampon device 10 allows a patient to breathe air through his/her nostrils while the patient's body works to stop bleeding at the nasal area. The intranasal tampon device 10 is not removed and reinserted until nasal bleeding has stopped. After recovery at the surgical center or hospital, nasal bleeding may still be active. The intranasal tampon device 10 remains in the nasal cavity during surgery, during recovery and after discharge. In discharging the patient, the portable adjustable disposable medical suction system 200 can be connected to the intranasal tampon device 10 to aspirate the blood or bodily fluid so that the patient can be discharged earlier despite continued nasal bleeding. The device 10 need not be connected to the central vacuum of the surgical facility. The portable, adjustable disposable medical suction system 200 enables the patient to manage the nasal bleeding at home.

In using the intranasal tampon device 10, blood or bodily fluid is absorbed into absorbent pads 12, 14 and aspirated into a collection container 16 while the patient breathes through breathing tubes 24a, b. It is contemplated that the various aspects discussed herein may be utilized with or without breathing tubes 24a, b. The blood or bodily fluid may be directed into the collection container 16 with a vacuum source 18. The inflatable cuff 46 is initially deflated and inserted into the nasal cavity of the patient along with the absorbent pads 12, 14 and the breathing tubes 24a, b. The inflatable cuff 46 may have a donut configuration with the breathing tubes 24a, b extending past the cuff 46. The inflatable cuff 46 is positioned so that upon inflation, the inflatable cuff 46 conforms to the inner walls of the choanae and forms a seal therebetween so as to occlude the passage to the throat and airway to prevent the flow of blood and other bodily fluids down the patient's throat or into the airway. Since the breathing tubes 24a, b extend past the cuff 46, the patient can breathe through the breathing tubes 24a, b while the cuffs 46 stop bodily fluid from flowing back through the throat and airway. During surgery and during recovery, the vacuum source 18, which is connected to the intranasal tampon device, may be a central vacuum source of a surgical center or hospital or an industrial pump (e.g., peristaltic pump). After being discharged from the surgical center or hospital, the intranasal tampon device 10 may be connected to the portable, adjustable disposable medical suction system 200 for aspirating bodily fluid from the nasal surgical site. The intranasal tampon device 10 and the portable, adjustable disposable medical suction system 200 are sufficiently small and light weight so that a patient 27 can utilize the device 10 at home or while on the move. The portable intranasal tampon device 10 reduces cost of care since the patient may be discharged earlier. The patient 27 may rest in the comfort of his/her own home while bleeding at the nasal area stops.

Figures 2, 2A:
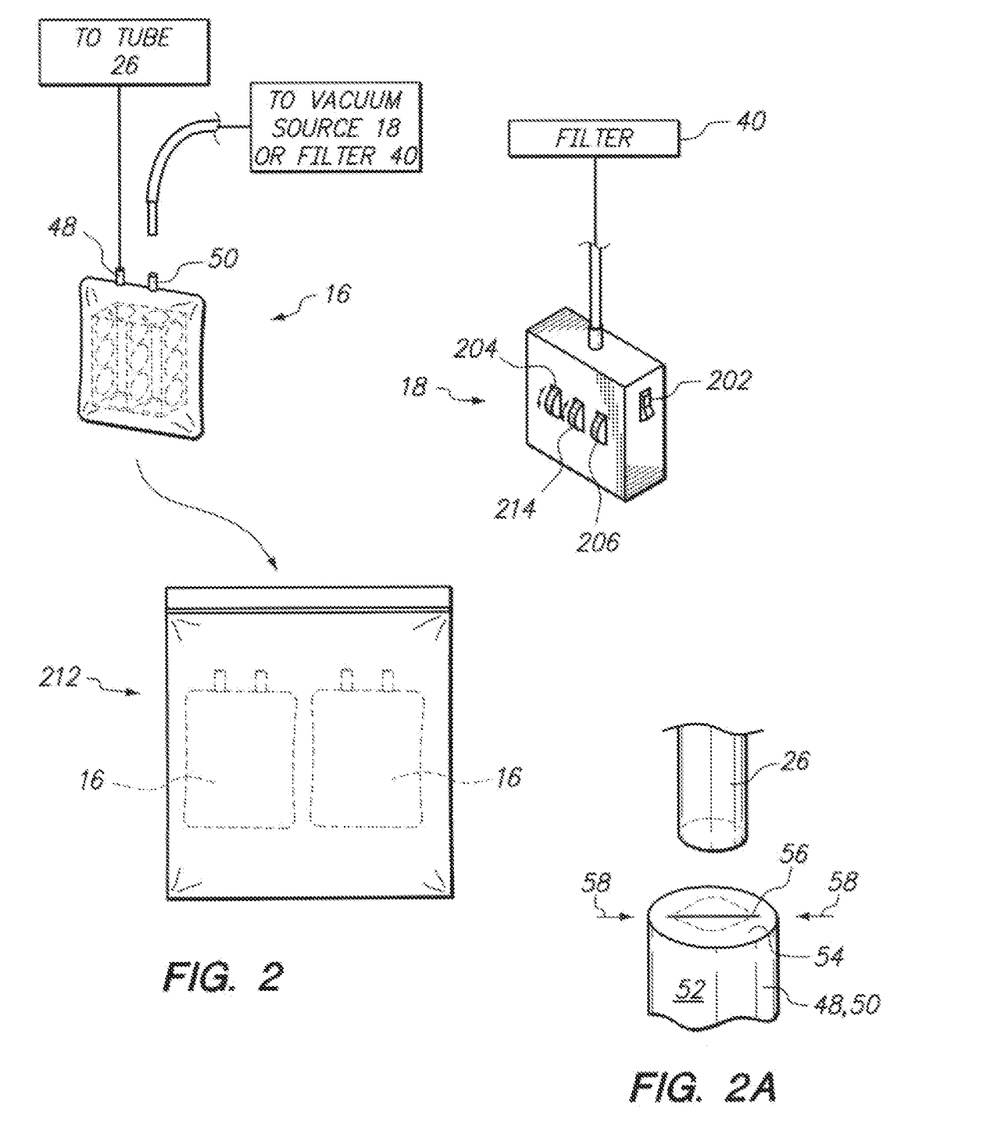
FIG. 2 is an enlarged view of the portable, adjustable disposable, medical suction system.
FIG. 2A is an enlarged view of an inlet or outlet of a collection container having a self-sealing opening.

More particularly, the portable, adjustable disposable medical suction system 200 is portable in that the system 200 is sufficiently lightweight so that the patient is still capable of enjoying regular hygiene, activity, diet and sleep after discharge from the surgical center or hospital. The system 200 includes a vacuum pump 18 which can be turned on and off with toggle switch 202. The vacuum pump can also be programmed to activate at regular intervals such as every 10, 20, or 30 minutes through adjustable control knob 204. Moreover, the strength of the vacuum created by the vacuum pump can be adjusted through adjustable control knob 206. The vacuum pump 18 can be battery operated so that the patient can easily change out the batteries if needed to maintain power to the vacuum pump.

The collection container 16 may be a flexible bag with an inlet 48 and an outlet 50. The tube 26 connected to the absorbent pads 12, 14 may be connected to the inlet 48. The vacuum source 18 may be connected to the outlet 50 of the collection container 16. When the vacuum pump 18 is on, bodily fluid is pumped into the collection container 16. When the collection container 16 is full, the collection container 16 may be detached from the tubes 26 connected to the vacuum source 18 and the absorbent pads 12, 14. The inlet 48 and the outlet 50 are self sealing so that upon removal of the tubes from the inlet 48 and the outlet 50, bodily fluid collected in the collection container 16 does not inadvertently spill out of the collection container 16. The collection container 16 may be stored in a red colored zip lock bag 212 for later disposal. The bag 212 can also be marked biohazard with instructions to dispose of the contents at the surgical center or hospital.

Referring now to FIG. 2A, the inlet 48 or outlet 50 of the collection container 16 is shown. The inlets and outlets 48, 50 of the collection container 16 may have a cylindrical wall 52 extending from the body of the collection container 16. The cylindrical wall 52 may be closed with a top surface 54 which may also have a self-sealing slit 56. To insert a tube 26 from the vacuum source or the absorbent pads 12, 14 into the inlet or outlet 48, 50, the user may squeeze the cylindrical wall 52 of the inlet or outlet 48, 50 in the direction of arrows 58. The arrows 58 line up with the slit 56 and cause the slit 56 to open up as shown in dash lines in FIG. 2A. When the slit 56 is spread open, the tube 26 can be inserted into the slit 56. Since the tube 26 is resilient and flexible and the top surface 54 is resilient and flexible, a liquid tight seal is formed between the outer surface of the tube 26 and the slit 56. The elastomeric nature of the top surface 54 causes the slit 56 to bear down on the outer surface of the tube 26 and form the liquid tight seal between the slit 56 and the tube 26. When detaching the tube 26 from the inlet 48 or outlet 50, the user may pull on the tube 26 until the tube 26 is extracted from the inlet 48 or outlet 50. When the tube 26 has been extracted from the inlet 48 or outlet 50, the elasticity of the top surface 54 causes the slit 56 to close up and form a liquid tight seal so that bodily fluid collected in the collection container 16 does not inadvertently spill out of the collection container 16. The collection container 16 may be a flexible plastic pouch. A mesh material or other porous support structure (e.g., open cell sponge or honey comb structure) may be disposed within the flexible plastic pouch so that the pouch does not collapse upon application of a vacuum pressure by the vacuum source 18. Rather, the mesh material or other porous support structure allows air to flow from the inlet 48 to the outlet 50 at all times.

The portable, adjustable disposable medical suction system 200 may be used in conjunction with the intranasal tampon device 10. The device 10 may have left and right lines 20, 22 for the left and right nostrils of the patient 27. The left line 20 may include the left absorbent pad 12. The absorbent pad 12 may have a breathing tube 24a which extends through the absorbent pad 12. When the absorbent pad 12 is inserted into the nasal cavity 26 of the patient 27, the breathing tube 24a enables the patient 27 to breathe through his/her nose so that the patient does not need to breathe through his/her mouth. The breathing tube 24a and the left pad 12 remain in place during surgery, during recovery and after discharge until the patient revisits the doctor for a follow up visit. Since the left pad 12 remains in place throughout the entire medical procedure until bleeding has ceased, pain and discomfort associated with dealing with the bodily fluid and bleeding at the nasal surgical site are minimized. The breathing tube 24a may be fabricated from a flexible material so that the breathing tube 24a may bend to conform to the anatomy of a nasal cavity 26 of the patient 27. When the absorbent pad 12 is inserted into the left nostril, one end of the breathing tube 24a may extend into the nasopharyngeal passageway (i.e., at the back of the throat) while the other end extends out of the nostril so as to enable the patient 27 to continue breathing through the nostril in which the absorbent pad 12 is installed. During surgery, the breathing tubes 24a, b extending out of the nostrils are initially long as shown in dash lines in FIG. 3 so that the distal end thereof is outside of the surgical field and the patient can breathe without interruption during surgery. After surgery, the breathing tubes 24a, b are cut short close to the patient's nostrils to promote patient comfort. Also, the cuff 47 is positioned and inflated to prevent bodily fluid from flowing back into the patient's throat and/or airway. After installation, the patient 27 continues to breathe through the breathing tube 24a during surgery, during recovery and after discharge until the doctor removes the pads 12, 14 and the breathing tubes 24a, b. The left absorbent pad 12 may be fabricated from an absorbent material which draws blood or bodily fluid from the nasal surface of the patient 27 through the absorbent pad 12. A suction tube 26a may have a distal end portion 28a which is disposed within the absorbent pad 12. The distal end portion 28a may have one or more apertures which are disposed within the left absorbent pad 12. Blood or bodily fluid that is absorbed into the left absorbent pad 12 during surgery, during recovery and after discharge is aspirated into the one more apertures formed in the distal end portion 28a of the suction tube 26a. Suction is created by the vacuum source 18. During, the surgery and recovery period, the vacuum source 18 is preferably the central vacuum source in the surgical center or hospital or an industrial sized vacuum source. After discharge, the vacuum source 18 is derived from the portable, adjustable disposable medical suction system 200. During the entire procedure from surgery to recovery, blood or bodily fluid is drawn away from the left absorbent pad 12 and into the suction tube 26a as shown by arrow 30.

Figure 3:
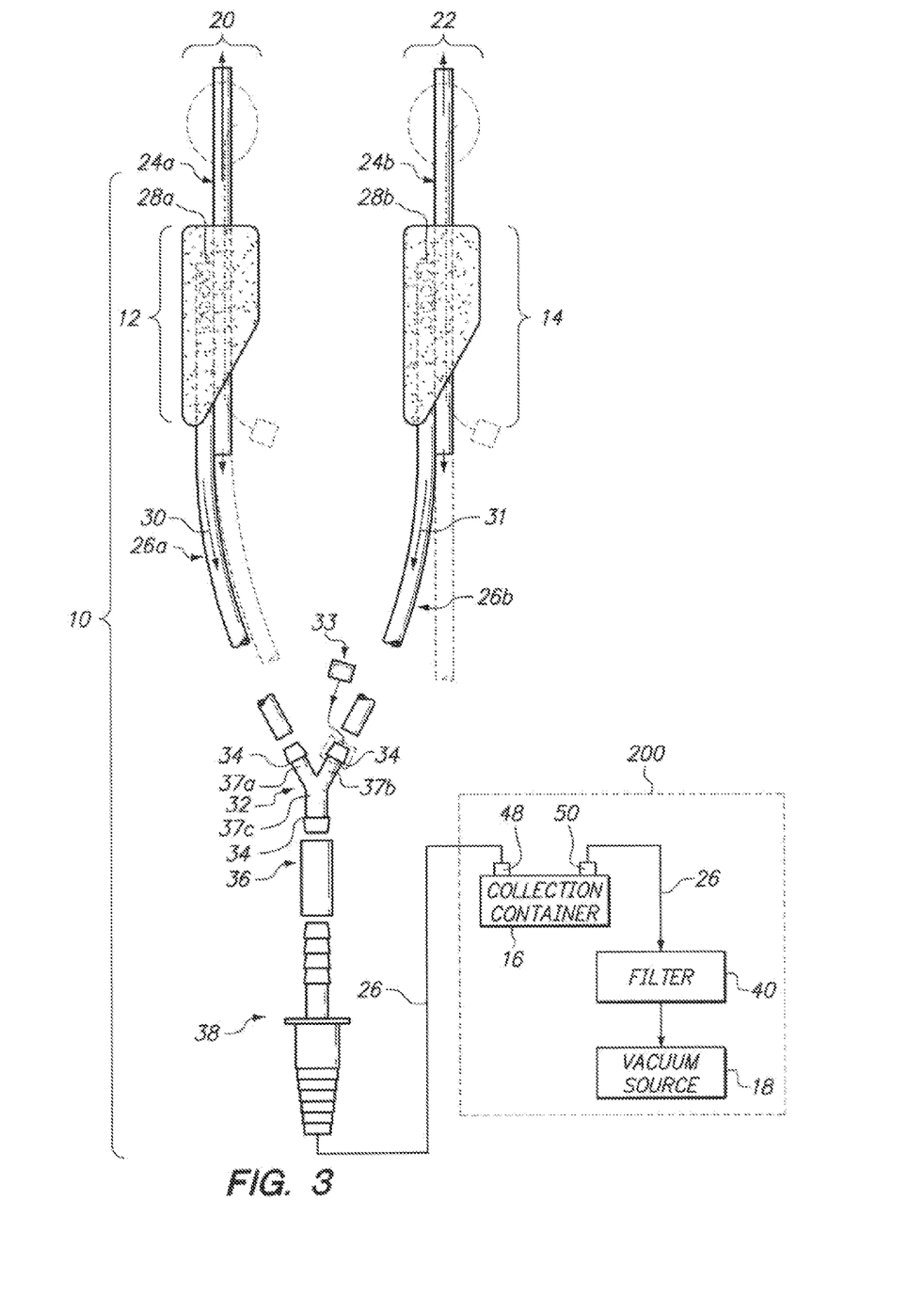
FIG. 3 is a schematic view of a first embodiment of the portable, adjustable disposable, medical suction system with a portable intranasal tampon device.

The right line 22 may include the tight absorbent pad 14. The right absorbent pad 14 may have a breathing tube 24b which extends through the right absorbent pad 14. When the absorbent pad 14 is inserted into the nasal cavity 26 of the patient 27, the breathing tube 24b enables the patient 27 to breathe through his/her nose so that the patient does not need to breathe through his/her mouth. The breathing tube 24b and the right pad 14 remains in place during surgery, during recovery and after discharge until the pattern 27 revisits the doctor for a follow up visit. Since the right pad 14 remains in place throughout the entire medical procedure until bleeding has ceased, pain and discomfort associated with dealing with the bodily fluid or bleeding at the nasal surgical she are minimized. The breathing tube 24b may be fabricated from a flexible material so that the breathing tube 24b may bend to conform to the anatomy of a nasal cavity 26 of the patient 27. When the absorbent pad 14 is inserted into the right nostril, one open end of the breathing tube 24b extends into the nasopharyngeal passageway (i.e., back of the throat) while the other open end extends out of the patient's 27 nostril so as to enable the patient 27 to continue breathing through the nostril in which the right absorbent pad 14 is installed. Also, the cuff 47 is positioned and inflated to prevent bodily fluid from flowing back into the patient's throat and/or airway. After installation, the patient 27 continues to breathe through the breathing tube 24b during surgery, during recovery and after discharge until the doctor removes the pads 12, 14 and the breathing tubes 24a, b. The right absorbent pad 14 may be fabricated from an absorbent material which draws blood or bodily fluid from the nasal surface of the patient 27 through the right absorbent pad 14. A suction tube 26b may have a distal end portion 28b which is disposed within the right absorbent pad 14. The distal end portion 28b may have one or more apertures which are disposed within the right absorbent pad 14. Blood or bodily fluid that is absorbed into the right absorbent pad 14 during surgery, during recovery and after discharge is aspirated into the one or more apertures formed in the distal end portion 28b of the suction tube 26b. Suction is created by the vacuum source 18. During surgery and recovery period, the vacuum source 18 is preferably the central vacuum source in the surgical center or hospital or an industrial sized vacuum source. After discharge, the vacuum source 18 is derived from portable, adjustable disposable medical suction system 200. During the entire procedure from surgery to recovery, blood or bodily fluid is drawn away from the right absorbent pad 12 and into the suction tube 26b as shown by arrow 31.

The left and light absorbent pads 12, 14 may be fabricated from surgical sponge such as a MEROCEL® type sponge, as commercially available from and manufactured by American Corporation, Mystic, Calif. Alternatively, the left and right absorbent pads 12, 14 may be fabricated from a super absorbent polymer. The left and right absorbent pads 12, 14 may be sized and configured to fit the gross contours of the nasal fossa. Moreover, prior to inserting the left and right absorbent pads 12, 14, a polymeric organic silicone compound may be lined to the exterior of the left and right absorbent pads 12, 14 which mitigates adherence of blood or other bodily fluid to the left and right absorbent pads 12, 14. Any type of anesthetic may be lined to the exterior surfaces of the left and right absorbent pad 12, 14. By way of example and not limitation, a XYLOCAINE gel may be lined to the exterior surfaces of the left and right absorbent pads 12, 14. Use XYLOCAINE gel also lubricates the left and right absorbent pads 12, 14 for easy insertion into the left and right nostrils of the patient 27 as well as provides a local anesthetic to desensitize the areas.

The breathing tubes 24a, b may be formed by infection molding from a compound such as MACLIN'S VM2800 and VM0400. Any conventional inert plasticizer such as adipate plasticizers or other phthalate esters can be used.

Figure 5:
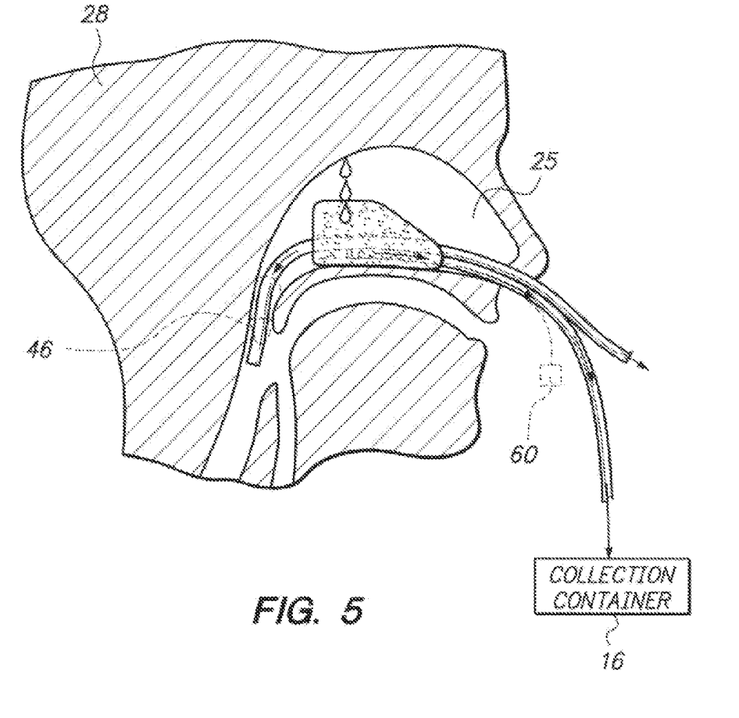
FIG. 5 illustrates insertion of absorbent pads of the portable intranasal tampon device into a nasal cavity of a patient to allow breathing through the nose while absorbing bodily fluid oozing out of a nasal surgical site.

As briefly discussed above, each of the left and right absorbent pads 12, 14 may also have an optional inflatable cuff 46 disposed behind the absorbent pads 12, 14. Referring to FIG 5, the optional inflatable cuff 46 shown in dash lines may be positioned so that upon inflation, the inflatable cuff 46 conforms to the inner walls of the channel and forms a seal therebetween so as to occlude the passageway and thereby prevent the flow of blood and other bodily fluids down the patient's throat and/or airway. The inflatable cuff 46 may be connected to a fluid valve 60. Upon insertion of the absorbent pads 12, 14, the valve 60 may be connected to a hypodermic syringe. The hypodermic syringe forces air or other fluid into the valve 60 and ultimately into the inflatable cuff 46 until a seal is formed to block passage to the patient's throat and stomach and also the airway of the patient. The tubes 24a, b extend past the curls 46 so that the patient can breathe through the tubes 24a, b while the cuffs 46 block back flow of bodily fluid into the throat and airway.

The intranasal tampon device 10 shown in FIG. 3 illustrates two lines 20, 22. However, if bleeding occurs solely or predominately only in one nostril, then one of the left or right lines 20, 22 may be removed. The Y connector 32 may be plugged with plug 33 so that the vacuum source 18 delivers a vacuum to the active one of the left and right lines 20, 22. The patient 27 or doctor may insert the active line 20 or 22 into the bleeding nostril so that the patient 27 may breathe through the breathing tube 24a or b of the active line 20 or 22 as well as the non-bleeding nostril.

When both lines 20 and 22 are active, each of the left and right lines 20, 22 May be inserted into the left and right nostril of the patient. The left and right absorbent pads 12, 14 fit the gross contours of the nasal fossa of the patient 27. The left and right suction tubes 26a, b may be attached to a Y connector 32. The Y connector 32 may have ridges 34. The tubes 26a, b are fitted over the branches 37a, b of the Y connector 32. The ridges 34 engage the interior surface of the suction tubes 26a, b to provide a liquid tight seal as well as to prevent the tubes 26a, b from inadvertently dislodging from the branches 37a, b of the Y connector 32. The bottom of the Y connector 32 has an additional branch 37c with ridge 34. The bottom branch 37c is connected to a single tube 36. The blood or bodily fluid is absorbed from the absorbent pads 12, 14, aspirated through tubes 26a, b and through the common tube 36. Connector 38 is connected to the tube 36, the collection container 16 and the vacuum source 18. The connector 38 may be connected to the inlet 48 of the collection container 16 with a tube 26 as described above. An outlet tube 26 is connected to the outlet 30 of the collection container 16. The outlet tube 26 is connected to the vacuum source 18 which provides suction through the system. A filter 40 may be disposed upstream of the vacuum source 18 and downstream of the collection container 16 to prevent blood or bodily fluid from entering the vacuum source 18. It is also contemplated that the filter 40 may be integrated into the outlet 50. The filter 40 allows gas (e.g., air) to flow through the filter 40 but not liquid (e.g., blood or bodily fluid). The filter 40 mitigates contamination of the vacuum source 18 from blood-borne contamination. The vacuum source 18 creates a vacuum to aspirate blood or bodily fluid out of the absorbent pads 12, 14 through tubes 26a, b and into the collection container 16.

During surgery and recovery at a surgical center or hospital, the vacuum source 18 may be a central vacuum source that is plumbed into the surgical center or hospital. The outlet 50 of the collection container 16 may be removably connected to the central vacuum source. When the patient 27 is discharged, the vacuum source 18 of the portable system 200 may be used. The system 200 may be packaged within a flexible or rigid housing. Throughout the entire process of surgery, recovery and discharge, suction is erected within the tubes 26a, b to aspirate bodily fluid. The blood or bodily fluid is aspirated out of the pads 12, 14 and transferred to the collection container 16. When the collection container 16 is full, the patient can remove the collection container and seal the collection container for storage and safe disposal at a convenient time for the patient. As discussed above, the collection container 16 can have self sealing inlets 48 and outlets 50 which seals the collection container 16 upon removal of the tubes 26 routed to the absorbent pads and the vacuum source 18. The collection container 16 with bodily fluid may be stored in a red colored bag 212. The patient or caregiver can call into the doctor to provide information regarding the bodily fluid collected such as color, consistency and quantity to determine whether the healing process is proceeding normally. Additional collection containers 16 can be re-attached to the tubes connected to the absorbent pads and vacuum source 18 as needed. If blood or bodily fluid is diverted toward the vacuum source 18, then the filter 40 may remove the blood/bodily fluid and allows only air to pass through the vacuum source 18. The filter 40 may be replaced on a periodic basis as needed.

After discharge from the surgical center or hospital, the portable, adjustable disposable medical suction system 200 can be connected to the intranasal tampon device 10 so that the patient can be discharged early from the surgical center or hospital despite continued nasal bleeding. The portable, adjustable disposable medical suction system 200 enables the patient to manage the nasal bleeding in the comfort of his/her own home. Upon activation of the portable, adjustable disposable medical suction system 200, a vacuum is created within the tubes 26a, b to aspirate fluid out of the absorbent pads 12, 14. As previously discussed, the vacuum source 18 may be programmable. By way of example and not limitation, the power or strength of the suction may be increased or decreased as desired by the user. The user can turn the control knob 206 to increase or decrease the suction strength of the vacuum pump 18. The vacuum pump 18 may also be programmed to be intermittently activated so that the vacuum source 18 is temporarily activated to drain blood or bodily fluid out of the absorbent pad 12, 14 when needed and turned off through manipulation of control knob 204. When the vacuum pump 18 is turned off, the absorbent pads 12, 14 absorb fluid until it has reached its maximum capacity. When needed or desired the patient 27 may manually activate the vacuum pump 18 through toggle switch 202 or program the vacuum pump 18 to intermittently activate through control knob 204. The intermittent operation of the vacuum source 18 may be controlled by way of the control knob 204 which increases or decreases the period of time that the vacuum source 18 remains deactivated. A third control knob 214 on the pump 18 may be used to increase or decrease the period of time that the vacuum pump 18 remains activated.

The portable vacuum source 18 may also be powered by a conventional AC electrical wall outlet. If so, then the patient 27 may rest at home or another location with an electrical outlet until nasal bleeding ceases.

Although an electrically operated vacuum pump 18 is described herein, it is also contemplated that the vacuum pump 18 may be a manual vacuum pump 18. The manual vacuum pump 18 may be operated by foot or hand. In this instance, when the absorbent pads 12, 14 are full of blood/bodily fluid or the nose bleed is irritating the patient 27, the patient 27 may pump the blood or bodily fluid out of the absorbent pads 12, 14 by manually actuating the manual vacuum pump 18. The manual vacuum pump 18 may also be a travel sized manual vacuum source. Moreover, the manual vacuum pump 18 may remain in fluid communication with the suction tubes 26a, b at all times. However, it is also contemplated that the manual vacuum pump 18 may be disconnected from the suction tubes 26a, b when the manual vacuum pump 18 is not in use. The manual vacuum pump 18 may be connected to the suction tubes 26a, b only when blood or bodily fluid needs to be drained out of the left and right absorbent pads 12, 14. The end of the tube to which the manual vacuum pump 18 is connected may be closed off with a plug when the manual vacuum source 18 is not being used to aspirate blood or bodily fluid out of the left and right absorbent pads 12.

The filter 40 which is placed immediately prior to the vacuum pump 18 or integrated with the outlet 50 of the collection container 16 may be a hydrophobic filter. The hydrophobic filter 40 allows gas such as air to pass therethrough but prevents the passage of liquid such as blood or bodily fluid. Accordingly, the hydrophobic filter protects the vacuum source 18 from contamination from the blood/bodily fluid or malfunction due to the fluid's entrance into the vacuum pump 18.

In use, the intranasal tampon device 10 may be used on a patient throughout a surgical procedure, namely, throughout surgery, recovery and alter discharge. Simply put, the device 10 is utilized during the entire process. The device 10 is not removed and reinstalled. Once installed, it remains in the nasal cavity of the patient until the patient has healed. Nasal surgery may cause extensive bleeding within the nasal cavity 25. During surgery, the device 10 removes blood/bodily fluid and prevents the blood/bodily fluid from entering the throat or wind pipe of the patient. Nasal bleeding may occur for an extended period of time. After surgery, the patient may be transferred to a temporary recovery room. From surgery to recovery, the device 10 (more particularly, the left and right pads 12, 14) remains in place to continue aspirating blood or bodily fluid from the nasal cavity. In discharging the patient 27, instead of waiting for the bleeding to stop at the surgical center or hospital the patient 27 may be discharged from the surgical center or hospital with a portable, adjustable disposable medical suction system 200 that provides continued portable suction force to the device 10. The left and right absorbent pads 12, 14 remain in the nasal cavity 25 or the left and right nostrils. Blood, mucous and other fluids around the surgical site are absorbed into the left and right absorbent pads 12, 14.

Figure 1:
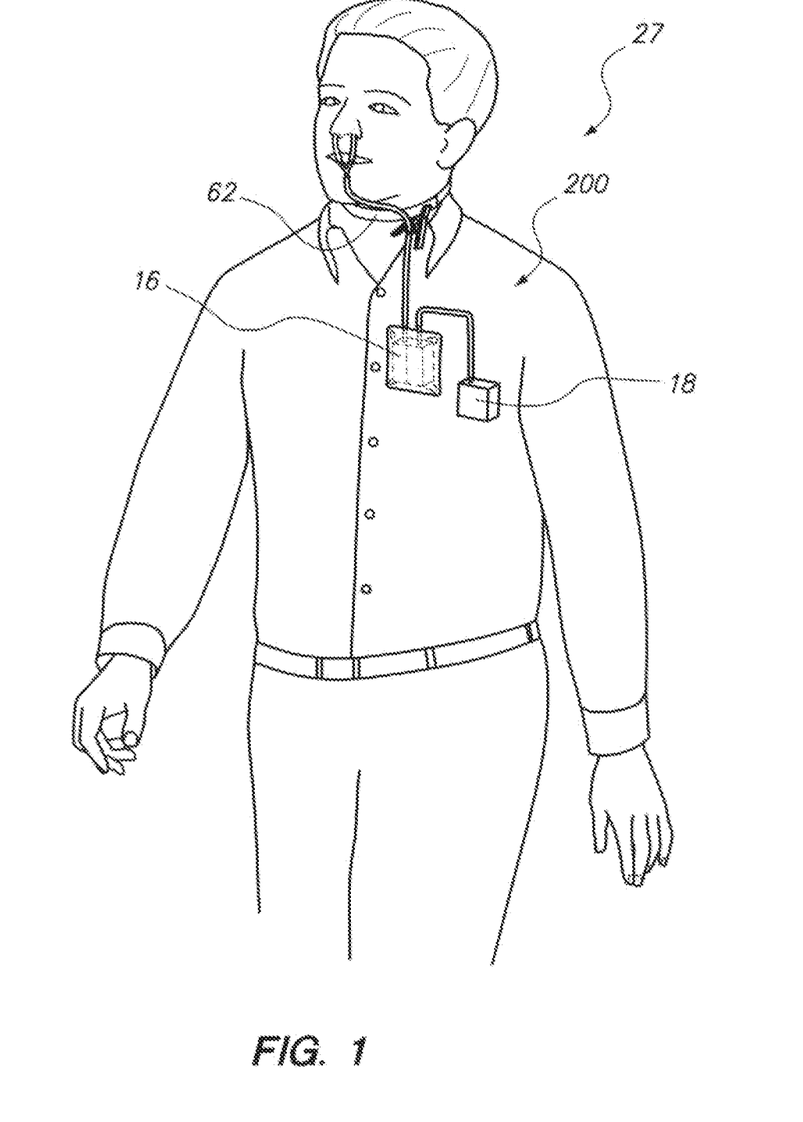
FIG. 1 illustrates a patient utilizing a portable, adjustable disposable, medical suction system with a nasal tampon device.

The breathing tubes 24a, b are sufficiently long so that a first distal open end of the tube 24a, b protrudes past the left and right absorbent pads 12, 14 into the nasopharyngeal passageway and opens to the back of the throat. A second distal open end of the tube 24a, b protrudes past the opposite side of the left and right absorbent pads 12, 14 and out of the patient's nostril. When the absorbent pads 12, 14 are inserted into the left and right nostrils of the patient, the first distal open ends of the breathing tubes 24a, b are disposed inside the nasopharyngeal passageway and opens to the back of the throat. The second distal open ends of the breathing tubes 24a, b are disposed outside of the nostrils of the patient 27. The breathing tubes 24a, b allow the patient to breathe through his/her nose while the absorbent pads 12, 14 absorb blood, mucous and other fluids during surgery, during recovery and after discharge until bleeding in the nasal cavity 25 ceases. The patient 27 can wear the portable intranasal tampon device 10 with the portable, adjustable disposable medical suction system 200 at home as shown in FIG. 1 to maintain mobility during waking hours and to allow the patient 27 to have a comfortable sleep at home. A strap 62 may be wrapped around the patient's neck. A clip which can be attached to the tubes 26 of the device 10 may be attached to the strap. The strap 62 and the clip are used to hold up the device 10 and prevent the weight of the portable intranasal tampon device 10 from pulling the device 10 out of the patient's nasal cavity. The strap 62 and the clip are shown being used adjacent to the patient's neck. However, it is contemplated that the strap and clip may be attached to other areas of the patient such as chest, arm, or waist. The collection container 16 and the vacuum pump 18 of the portable, adjustable disposable medical suction system 200 may be clipped to the patient's 27 belt or shirt as shown. The portable, adjustable disposable medical suction system 200 allows the patient 27 to have greater mobility soon after surgery, reduces patient 27 medical expenses and reduces hospital stays. During sleeping hours, the patient 27 may also utilize the intranasal tampon device 10 with the portable, adjustable disposable medical suction system 200 to breathe normally and not be irritated by dripping blood or bodily fluid into the patient's 27 throat or wind pipe.

Figure 4:
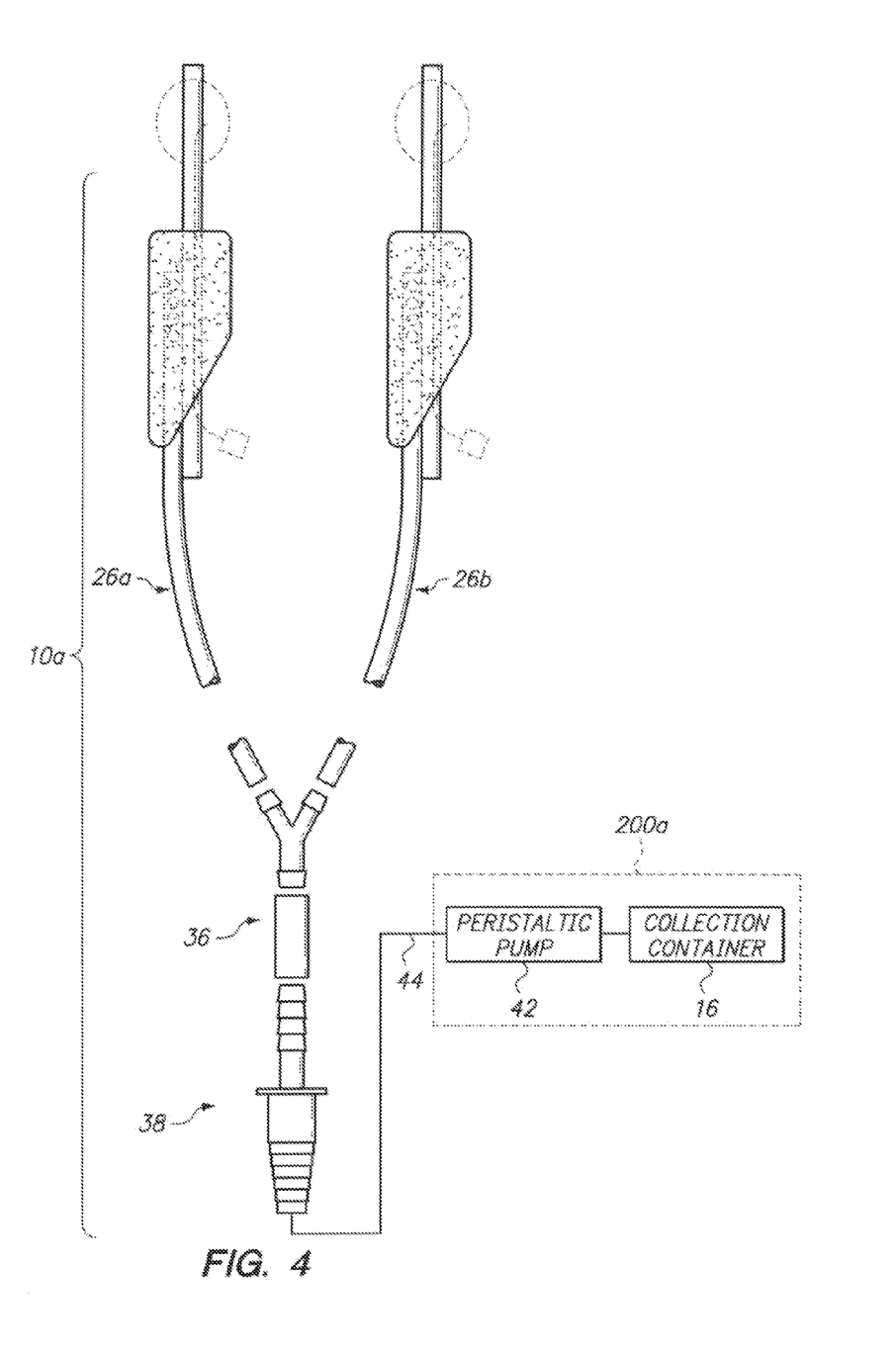
FIG. 4 is a second embodiment of the portable, adjustable disposable, medical suction system with portable intranasal tampon device.

Referring now to FIG. 4, an alternate embodiment of the portable, adjustable disposable medical suction system 200 is shown. The second embodiment of the portable, adjustable disposable medical suction system 200a may incorporate the features discussed above in relation to the first embodiment. However, the second embodiment of the portable, adjustable disposable medical suction system 200a may utilize a peristaltic pump 42. In this instance, no filter 40 is utilized. Additionally, the peristaltic pump 42 is located upstream of the collection container 16. The connector 38 is connected lo a resilient tube 44 which is fed through the peristaltic pump 42 and connected to the collection container 16. Rollers of the peristaltic pump 42 flow the blood or bodily fluid through the tubes 26a, b, 36 and 44 into the collection container 16. Since the rollers of the peristaltic pump 42 only contacts the exterior of the tube 44 and the nasal fluid (e.g., blood, mucous and other fluids) contact only the interior of the tube 44, no filter is required. The entire portable, adjustable disposable medical suction system 200a except the peristaltic pump 42 is disposable. The peristaltic pump 42 may be powered with electricity from an electrical outlet. As such, the device 10a may be utilized off-site at the patient's 27 home or other fixed location outside of the hospital. The collection container 16 in this example may have an optional air vent.

The portable, adjustable disposable medical suction system 200 and the intranasal tampon device 10, 10a may be disposable. For example, after the patient's 27 nasal cavity stops bleeding, the portable intranasal tampon device 10, 10a may be discarded or recycled as desired. Reusable components such as the peristaltic pump 42 may be returned to the provider.

The portable, adjustable disposable medical suction system 200 have been described in conjunction with an intranasal tampon device 10 to arrest nasal bleeding after surgical procedures. However, the portable, adjustable disposable medical suction system 200 may be used in conjunction with the intranasal tampon device 10 may be utilized by individuals that have a persistent nose bleed. Moreover, the portable, adjustable disposable medical suction system 200 has been described in relation to nasal surgery. The portable, adjustable disposable medical suction system 200 intranasal tampon devices 10 and 10a have been described as absorbing blood or bodily fluid from the nasal area. However, the intranasal tampon devices 10, 10a and the portable, adjustable disposable medical suction system 200 may absorb other fluids such as mucous and other bodily fluids generated in the nasal cavity which prohibits or make breathing difficult through the nostrils for the patient 27. This bodily fluid is aspirated into the collection container 16 as described above.

Figure 6:
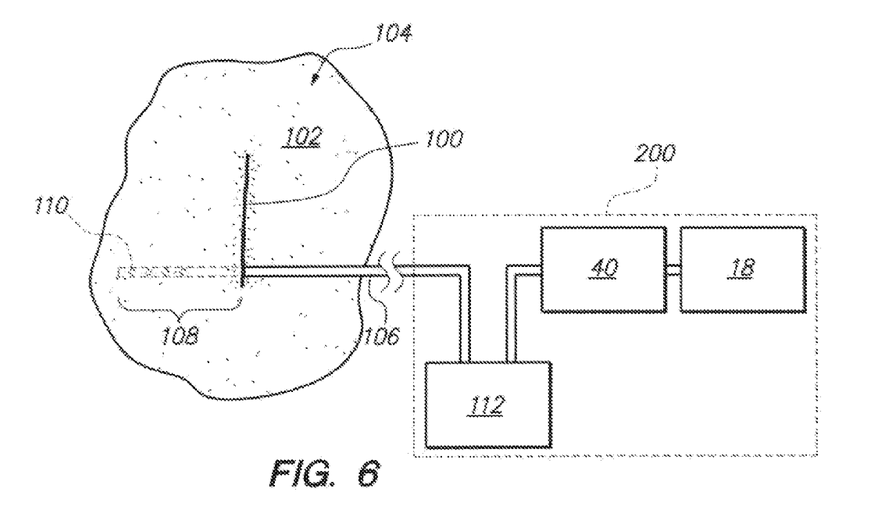
FIG. 6 illustrates a patient with the portable, adjustable disposable, medical suction system used to aspirate bodily fluid from a surgical site.

The portable, adjustable disposable medical suction system 200 discussed above has many other applicational uses. By way of example and not limitation, the portable, adjustable disposable medical suction system 200 may be utilized to withdraw blood or bodily fluid from internal bleeding caused by surgery or trauma as shown in FIG. 6. In particular, the surgical site of a patient 27 may have an opening 100 through a skin 102 of the patient 27 at the surgical site 104. An elongate tube 106 may be disposed in the opening 100 at the surgical site. A distal portion 108 of the elongate tube 100 may have a plurality of apertures 110. The distal portion 108 is disposed under the skin 102 of the patient 27 at the surgical site 104. The opening 100 may be closed with a dermabond, suturing or other techniques known in the art or developed in the future. The tube 100 extends into the body of the patient 27 and extends out of the body of the patient 27. The portion of the tube 106 which extends out of the body of the patient 27 is connected to a collection container 112 and the portable vacuum source 18. The portable vacuum source 18 draws blood/fluid out of the body of the patient 27 through the apertures 110, through the tube 106 and into the collection container 112. The collection container 112 is removably attachable to the tube 106. The collection container 112 may be sealable (e.g., resealable zipper such as a ZIPLOC bag) so that after removal from the tube 106 when the collection container is full, the bodily fluid (e.g., blood, moisture, etc.) can be stored in the collection container until it can be safely discarded at the hospital, outpatient care center or otherwise safely discarded. Additional collection containers can be attached to the tube 106 if more blood or bodily fluid needs to be aspirated from the surgical site. The portable vacuum source 18 may be a battery operated vacuum source 18 so that the patient 27 can be discharged from the hospital or outpatient surgical center with the device and recuperate at home.

Figure 7:
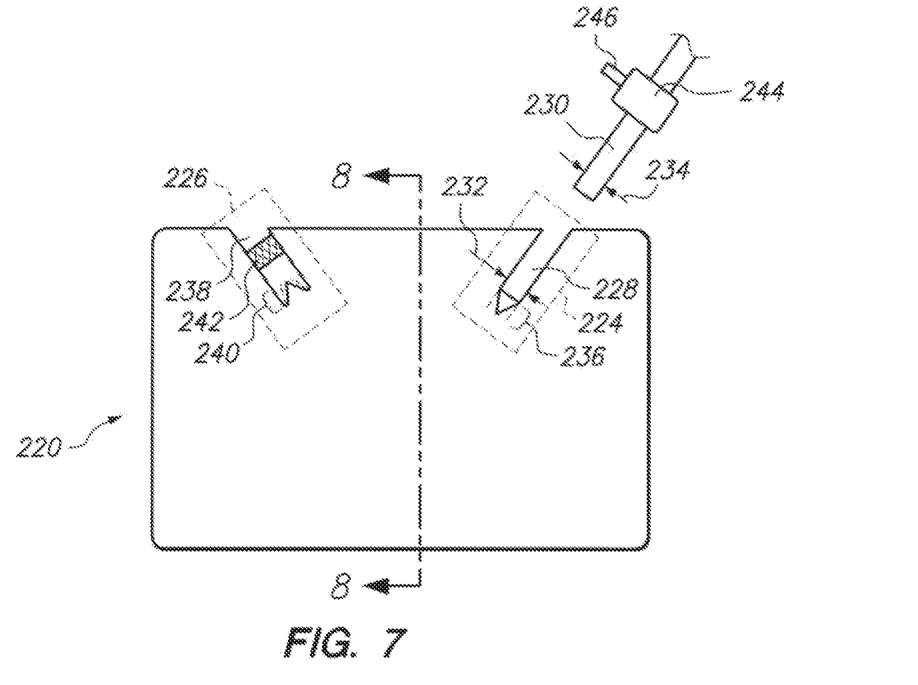
FIG. 7 illustrates use of a container in a closed system.
Figure 8:
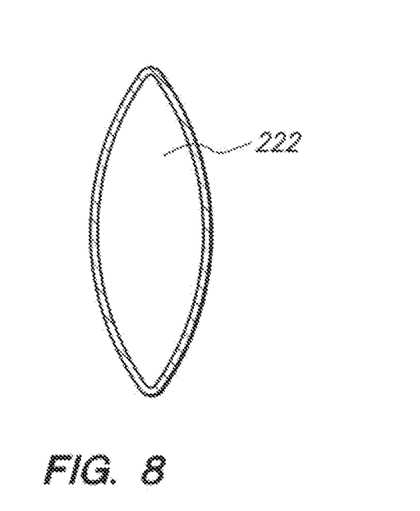
FIG. 8 is a cross sectional view of the container shown in FIG. 7.
Figure 9:
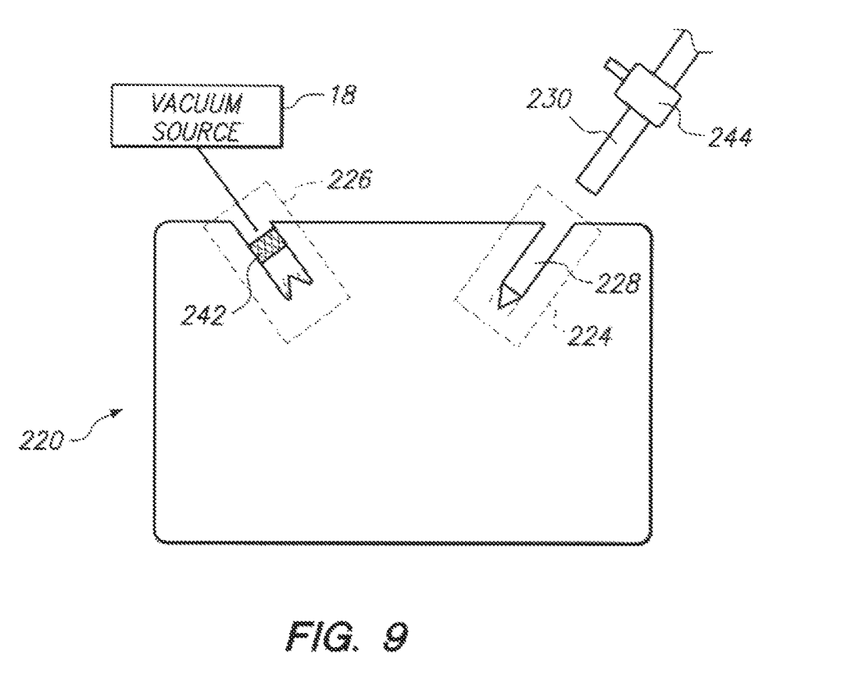
FIG. 9 illustrates use of the container in an open system.

Referring now to FIGS. 7-9, a collection container 220 that may be utilized in an open system or in a closed system is disclosed. The collection container 220 is disposable, and thus sanitary for the patient and medical professional. An example of the open system is nasal surgery discussed in relation to FIGS. 1-5. The vacuum source 18 pulls both bodily fluid and air from the atmosphere into the container 16. An example of the closed system is the invasive medical procedure discussed in relation to FIG. 6. Here, the vacuum source 18 does not draw air from the atmosphere into the container 112. The vacuum source 18 draws only bodily fluids from the inside of the patient.

More particularly, referring now to FIGS. 7 and 8, the container 220 may be fabricated from a resilient material that is bendable and flexible. The container 220 is formed so that in its natural state, the walls of the container 220 are expanded outward and define an interior cavity 222. The container 220 may be compressed by a person's hand and when released, the walls of the container 220 expand outward back to its normally outward biased state. The front view of the container 220 shown, in FIG. 7 may have a rectangular or square configuration. However, a side view of the container 220 shown in FIG. 8 indicates that the container 220 may have an oval configuration. A person may grip the container 220 and squeeze the walls of the container 220 down so that a volume of the interior cavity 222 is reduced. Upon release of the container 222, the resiliency of the walls of the container 220 urges the container 220 back to its original expanded shape. The expansion of the walls of the container 220 creates a vacuum within the interior cavity 222. The walls of the container 220 may be fabricated from an elastomeric material, a plastic material, or any other material that is resilient and causes the walls of the container 220 to expand outward after the container 220 is compressed and released.

FIGS. 7 and 8 illustrate use of the container 220 in relation to a closed system. In particular, the container 220 is utilized to ensure all bodily fluid from the patient is drawn out of the patient's body and urged into the container 220. When the person squeezes the container 220 to reduce the volume of the cavity 220 and releases the container 220, the resiliency of the walls of the container 220 creates the vacuum within the container 220. The container 220 is in fluid communication to the wound. The vacuum within the interior cavity 222 of the container 220 is applied to a tube 230 that connects the container 220 to the wound.

The container 220 additionally has an input port 224 and an output port 226. The input port 224 has a receptacle 228. This receptacle 228 is sized and configured to form an airtight seal with the tube 230 which is in fluid communication with the wound of the patient. By way of example and not limitation, the receptacle 228 may be formed as a cylindrical hole. A diameter 232 of the cylindrical hole defining the receptacle 228 may be slightly smaller than a diameter 234 of the tube 230. In this manner, when the tube 230 is inserted into the receptacle 228, the exterior surface of the tube 230 contacts and provides a tight fit with the internal surface of the receptacle 228. Although the receptacle 228 is shown and described as a cylindrical hole, other shapes for the receptacle 228 are also contemplated. By way of example and not limitation, the receptacle 228 may have a funnel shape, rectangular shape, oval-shape or any other shape that achieves an airtight seal with the tube 230. Additionally, the receptacle 228 may be retrofitted with a connector that can receive the tube 230 and form an airtight and liquid tight seal therewith.

Figure 7A:
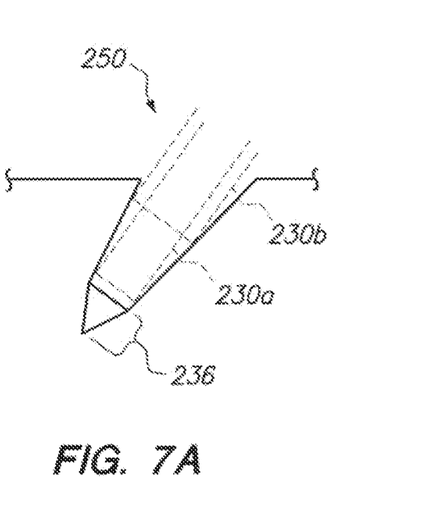
FIG. 7A is an enlarged sectional view of the container shown in FIG. 7.

The funnel shaped receptacle 228 is shown in detail in FIG. 7A. As shown, the funnel shape has a wider opening 250 compared to the distal end near the one way valve 236. In this manner, the receptacle 228 may receive different diameter sizes of tubes 230. A small diameter tube 230a may be received in and form an airtight and liquid tight seal with the receptacle 228. A larger diameter tube 230b may be received in and form an airtight and liquid tight seal with the receptacle 228. Although not shown, the receptacle 238 of the output port 226 may also have a funnel shape for receiving and forming an airtight and liquid tight seal with a number of tubes having different diameters.

The input port 224 may additionally have a one-way valve 236. The one-way valve 236 allows fluid to be transferred from outside of the container 220 into the cavity 222. However, the one-way valve 236 at the input port 224 prevents fluid from being transferred from inside of the container 220 to the outside of the container 220. In the example shown, the one-way valve 236 allows bodily fluid to be transferred from the patient or person to the internal cavity 222. When the tube 230 is removed from the receptacle 228, the one-way valve 236 prevents the bodily fluid contained within the container 220 from flowing out of the input part 224.

The output port 226 also has a recess 238. The output port 226 also has a one-way valve 240 that allows fluid to escape from the internal cavity 222 of the container 220 to the atmosphere. However, the output port 226 additionally has a hydrophilic or a hydrophobic filter 242. The filter 242 allows gas such as air to escape from the internal cavity 222 into the atmosphere but does not allow liquid (e.g., bodily fluid) to pass through the filter 242. The recess 238 may have a cylindrical hole configuration. However, other configurations are also contemplated. By way of example and not limitation, the recess 238 may have a funnel shape, rectangular shape, oval-shape or any other shape. When the container 220 is used for the closed system, the recess 238 merely acts as an output exhaust. However, when the container 220 is used for an open system, the recess 238 is connected to the vacuum source 18. In this instance, the recess 238 is sized and configured to form an airtight and liquid tight seal with the fluid communication line to the vacuum source 18. As will be discussed below, in this instance, the recess 238 may have other configurations for achieving such liquid tight and airtight seal.

The tube 230 connected to the input port 224 may additionally have a pinch valve 244. The pinch valve 244 allows the person to shut off fluid flow through the tube 230. When the pinch valve 244 is on, no fluid passes through the tube 230. When the pinch valve 244 is off, fluid can freely pass through the tube 230. The pinch valve 244 may be operated by actuating a lever 246 to turn the pinch valve 244 on or off. By way of example and not limitation, the pinch valve 224 may operate so as to have a shut off mechanism disposed within the tube 230. To turn the pinch valve 244 on or off, the mechanism disposed within the tube 230 may be rotated or shifted 90 degrees. This may be accomplished by means known in the art or developed in the future such as through mechanical linkages or magnetism. In another example, the pinch valve 224 may be a simple clamp that compresses the tube 230 by actuation of a handle.

To utilize the container 220 in a closed system such as when draining bodily fluid from an invasive surgical procedure, the container 220 is initially compressed. A person (e.g., medical professional or patient) squeezes the container 220 to reduce the size of the internal cavity 222. Air within the internal cavity 222 is forced out of the output port 226 through the one-way valve 240. With the pinch valve 244 on so that no fluid passes through the tube 230 and the person continuing to squeeze or compress the container 220, the distal end portion of the tube 230 is inserted into the receptacle 228. The tight fit between the receptacle 228 and the tube 230 forms an airtight or liquid tight seal therebetween. When the person releases the container 220, gas is not allowed to flow through the tube 230 since the pinch valve 244 is turned on. Moreover, gases are not allowed to flow through the output port 226 into the internal cavity 222 because of the one-way valve 240. A vacuum is formed in the interior cavity. The container 220 remains compressed even though the person releases the container 220.

The other end of the tube 230 is disposed within the body of the patient at the wound site to drain any bodily fluid that might be produced because of the wound. The end of the tube 230 disposed within the patient's body may have a plurality of holes 110 as shown in FIG. 6. The opening of the wound is sealed off so that air does not enter the holes 110 and destroys the vacuum. Hence, the container 220 is being utilized in a closed system.

The pinch valve 244 is now turned off so that fluid can flow through the tube 230. The vacuum created by the compressed container 220 draws bodily fluid from the wound into the internal cavity 222 of the container 220. As a container 220 expands out, the bodily fluid is drawn into the container 220. As the container 220 continues to expand outward, the vacuum pressure created by the container 220 decreases. At a certain point in time, the vacuum created by the container 220 is insufficient to draw bodily fluid from the patient or the container 220 is fully expanded outward and no vacuum is created.

When the vacuum created by the container 220 is absent or insufficient to draw bodily fluid from the wound of the patient into the container 220, the container 220 may be changed out with a new container 220 in the following manner. The pinch valve 246 is turned on by actuating lever 246. At this point, no fluid is allowed to pass through the tube 230. The tube 230 is removed from the receptacle 228. The one-way valve 236 of the input port 224 prevents the bodily fluid within the container 220 from leaking out of the container 220. Moreover, the filter 242 at the output port 226 prevents the bodily fluid from leaking out of the container 220 through the output port 226. The used container 220 is placed in a red bag and sealed for disposal.

A new container 220 is connected to the tube 230. In particular, the person squeezes the new container 220. Air is allowed to escape out of the output port 226 through the one-way valve 240. The person connects the tube 230 into the receptacle 228 of the input port 224. A tight fit between the tube 230 and receptacle 228 creates a liquid and airtight seal therebetween. When the person releases the container 220, a vacuum is created within the container 220. The pinch valve 244 is now activated to the off position to allow fluid to flow through the tube 230. Bodily fluid then continues to flow into the container 220 until desired or until the body no longer produces bodily fluid. The container 220 may be replaced as desired or prescribed by a medical professional.

An alternate method of connecting a container 220 to the tube 230 is disclosed herein. The container 220 is compressed or squeezed after connecting the tube 230 to the input port 224. In particular, with the pinch valve 244 activated so that no fluid passes through the tube 230, the tube 230 is engaged to the input port 224 to form an airtight and liquid tight seal therebetween. The user does not need to compress the container 220 prior to connecting the tube 230 to the input port 224. Rather, after connecting the tube 230 to the input port 224, the user may compress the container 220. Air within the container 220 does not flow back into the tube 230 due to the one-way valve 236. Also, the pinch valve 244 is activated so that no fluid passes through the tube 230. The air within the internal cavity 222 of the container 220 flows out of the container 220 through the output port 226. When the user releases the container 220, a vacuum is created because no air is allowed back into the container 220 through the output port 226. The one-way valve 240 prevents air from entering the container 220 from the output port 226. The pinch valve 244 is now deactivated so that fluid flows through the tube 230. The vacuum created within the container 220 is applied to the tube 230 and bodily fluid is drawn from the patient into the container 220. In this discussion, the container 220 was compressed prior to deactivating the pinch valve 244. However, it is also contemplated that the container 220 may be compressed after deactivating the pinch valve 244.

As discussed herein, the holes 110 formed in the tube 230 are disposed within the body of the patient. Sometimes, accidentally, the hole 110 closest to the wound opening slips out and is exposed to the atmosphere. In this event, the container 220 would lose the vacuum since air would rush into the container 220. However, it is contemplated that the hole that is exposed to the atmosphere may be taped up or closed with tape to reestablish the closed system (i.e., air tight system). By way of example and not limitation, after the tube 230 is disposed within the patient's body, the patient may move around to eat, use the restroom, drive, etc. While moving around, the tube 230 may be pulled out by accident and expose the proximal hole 110 to the atmosphere. If the vacuum is lost in the container 220, the user or medical professional may tape up the proximal hole 110 to seal such hole. The medical professional or user may slightly squeeze the container 222. Air and bodily fluid does not flow back into the input port 224 because of the one-way valve 236. Only air is allowed to escape out of output port 226. Any bodily fluid within the container 220 does not escape out of the output ports 226 due to the hydrophilic or hydrophobic filter 242. Once the desired compression of the container 220 is achieved, the user or medical professional releases the container 222 to produce the vacuum within the container 220 and to continue drawing bodily fluid from the patient through the tube 230.

Referring now to FIG. 9, the container 220 may be utilized in an open system such as in nasal surgery discussed above. To utilize the container 220 in an open system, the container 220 need not be compressed as in the closed system discussed in relation to FIGS. 7 and 8. Rather, the lube 230 is merely connected to the receptacle 228 of the input port 224. With the tube 230 connected to the receptacle 228, the pinch valve 244 is switched to the off position to allow fluid to flow through the tube 230. Next, the vacuum source 18 is connected to the output port 226. When the vacuum 18 is activated or turned on, the vacuum source 18 creates a vacuum within the container 220. Such vacuum draws the bodily fluid from the patient. Moreover, since this is an open system, air and ambient gas are also flowed into the tube 230. The bodily fluid drips into the container 220 but is not allowed to flow into the vacuum source 18 due to the hydrophilic or hydrophobic filter 242. The receptacle 228 may have a cylindrical hole configuration. However, other configurations are also contemplated such a funnel shape, rectangular shape, oval-shape, etc. Other shapes may be utilized for the receptacle 228 so long as the shape of the receptacle 228 is conducive to forming an airtight and liquid tight seal with the fluid communication line to the vacuum source 18.

As discussed above, the container 220 is compressible but yet resilient in that it resumes its original outward expanded shape after being compressed and released, as shown in FIGS. 7 and 8. The resiliency of the container 220 is sufficient to withstand the vacuum created by the vacuum source 18 so that upon application of the vacuum by the vacuum source 18, the container 220 does not significantly collapse. Preferably, the vacuum source 18 only creates a slight reduction in the internal cavity 222, if at all.

When the container 222 is filled up, the container 220 is replaced. The pinch valve 244 is turned on to stop flow of fluid through the tube 230. The tube 230 is removed from the receptacle 228 as is the connection of the fluid communication line of the vacuum source 18 to the output port 226. The used container 220 is placed in a red bag and sealed for disposal. The vacuum source 18 is reconnected to the output port 226 of the new container 220. Also, the tube 230 is inserted into the receptacle 228 of the new container 220. The pinch valve 244 is turned off to allow fluid to flow through the tube 230. The vacuum source 18 is now turned on to create a vacuum in the container 220 to re-start drawing bodily fluid into the container 220.

The above description is given by way of example, and not limitation. Given the above disclosure, one skilled in the art could devise variations that are within the scope and spirit of the invention disclosed herein, including various ways of connecting the first and second lines to the vacuum source 18. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A bodily fluid container for collecting bodily fluid drained from a patient, the container comprising:
    a resilient compressible body defining an interior cavity and a volume of the interior cavity capable of being reduced and operative to form a negative pressure as the resilient body expands from a compressed state to an uncompressed state;
    an input port formed on the resilient compressible body at a first end of the resilient compressible body, the input port having:
        an input receptacle configured to form a liquid tight seal with a first end of a tube having a second end in fluid communication with the patient to provide fluid communication from the patient to the container;
        a one way valve disposed in the input port for allowing fluid to flow into and not out of the interior cavity;
    an output port formed on the resilient compressible body at the first end of the resilient compressible body, the output port having:
        an output receptacle;
        a one way valve disposed in the output port for allowing fluid to flow out of and not into the interior cavity;
        a gas permeable and liquid non-permeable member for allowing gas to flow through the output port and not bodily fluid, wherein the output receptacle is configured to provide an airtight seal with a line to a vacuum source.

2. The container of claim 1 wherein the input receptacle is a recess formed in an upper portion of the body having a cylindrical configuration, and the recess of the input receptacle is sized to receive a tube connectable to a patient.

3. The container of claim 1 wherein the gas permeable and liquid non-permeable member is a hydrophilic material.

4. The container of claim 1 wherein the input receptacle has a cylindrical hole configuration.

* * * * *